(12) United States Patent
Nunez Lopez et al.

(10) Patent No.: US 11,936,070 B2
(45) Date of Patent: Mar. 19, 2024

(54) SYSTEM AND METHOD FOR A WEARABLE CIRCUIT

(71) Applicant: Bloomer Health Tech Inc., Cambridge, MA (US)

(72) Inventors: Carlos Nunez Lopez, Cambridge, MA (US); Bethany VanWagenen, Somerville, MA (US); Alicia Chong Rodriguez, Somerville, MA (US)

(73) Assignee: Bloomer Health Tech Inc., Cambridge, MA (US)

( * ) Notice: Subject to any disclaimer, the term of this patent is extended or adjusted under 35 U.S.C. 154(b) by 427 days.

(21) Appl. No.: 17/373,122

(22) Filed: Jul. 12, 2021

(65) Prior Publication Data
US 2022/0013869 A1    Jan. 13, 2022

Related U.S. Application Data

(60) Provisional application No. 63/050,468, filed on Jul. 10, 2020.

(51) Int. Cl.
*H01M 50/521* (2021.01)
*A41C 3/00* (2006.01)

(52) U.S. Cl.
CPC ........... *H01M 50/521* (2021.01); *A41C 3/005* (2013.01)

(58) Field of Classification Search
CPC .... A41C 3/005; D03D 1/0035; D03D 15/247; D03D 15/267; D03D 15/513; D04B 1/14; D04B 1/225; D04B 21/205; D04B 1/102; H05K 1/14; H05K 3/36; H05K 1/028; H05K 1/0283; H05K 2201/09236; H05K 2201/09263; H05K 2201/10037; H05K 2203/1322; H05K 3/305
See application file for complete search history.

(56) References Cited

U.S. PATENT DOCUMENTS

| | | | |
|---|---|---|---|
| 8,192,863 B2 | 6/2012 | Best et al. | |
| 8,664,571 B2 | 3/2014 | Macher et al. | |
| 9,343,716 B2* | 5/2016 | Rothkopf | H01L 31/048 |
| 9,564,761 B2 | 2/2017 | Hopfer, III et al. | |
| 9,735,443 B2 | 8/2017 | Takahashi et al. | |
| 9,947,905 B2 | 4/2018 | Keates | |
| 10,090,556 B2 | 10/2018 | Rho et al. | |
| 10,381,607 B2 | 8/2019 | Shin et al. | |
| 10,461,306 B2 | 10/2019 | Marmaropoulos et al. | |
| 2016/0301044 A1 | 10/2016 | Huang et al. | |
| 2018/0226629 A1 | 8/2018 | Hiroki et al. | |

(Continued)

FOREIGN PATENT DOCUMENTS

CN   208690415 U   4/2019

*Primary Examiner* — Krystal Robinson
(74) *Attorney, Agent, or Firm* — Caldwell Intellectual Property Law

(57) ABSTRACT

A system for a wearable circuit is described. The system includes a soft substrate. The system include a first battery assembly attached to the soft substrate. The system includes a second battery assembly attached to the soft substrate. The system includes a flexible connecting device. A flexible connecting device is configured to connect a first battery assembly to a second battery assembly and stretch along a path of a soft substrate. A flexible connecting device provides an electrical connection between a first and second battery assembly while being stretched.

20 Claims, 12 Drawing Sheets

(56) References Cited

U.S. PATENT DOCUMENTS

2019/0090350 A1     3/2019   Kumar
2020/0127245 A1     4/2020   Fan et al.
2020/0287240 A1*    9/2020   Hudak .............. H01M 10/0525

* cited by examiner

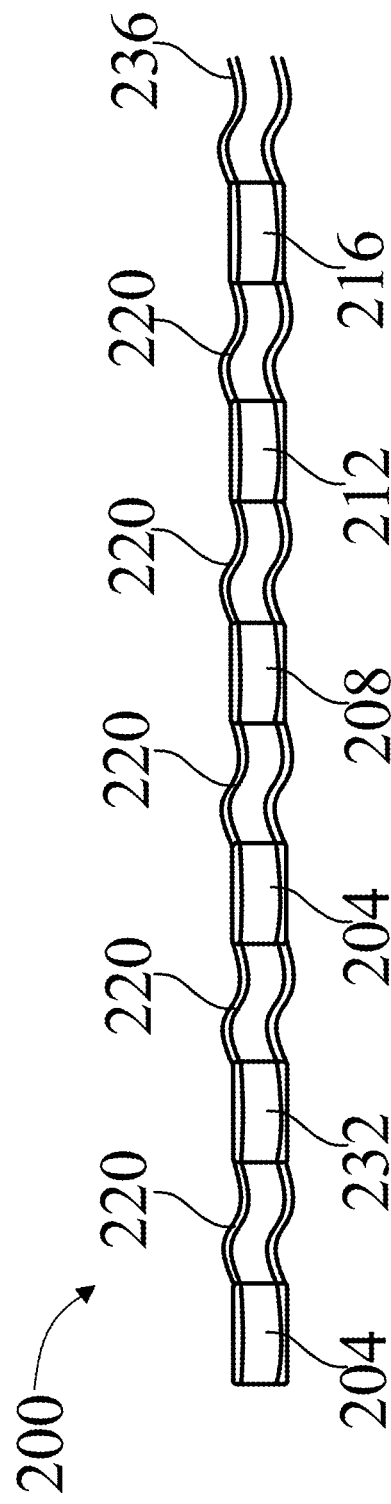
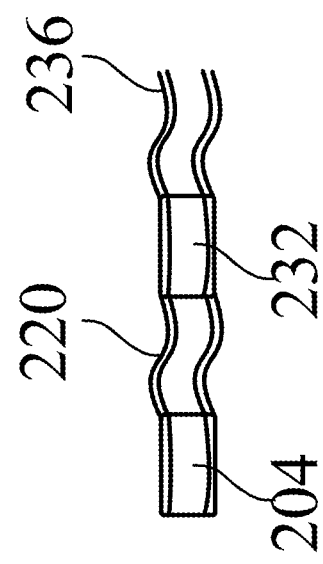
FIG. 2A
FIG. 2B

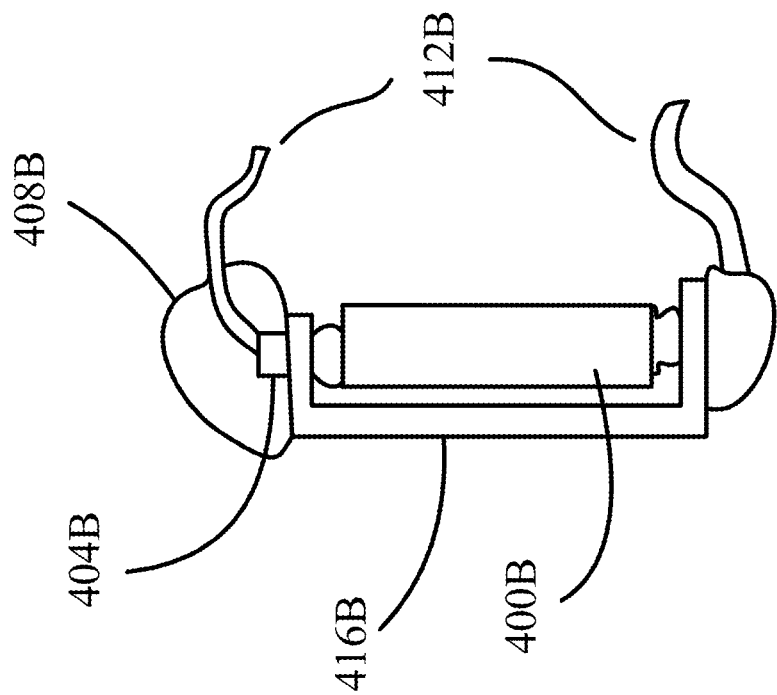
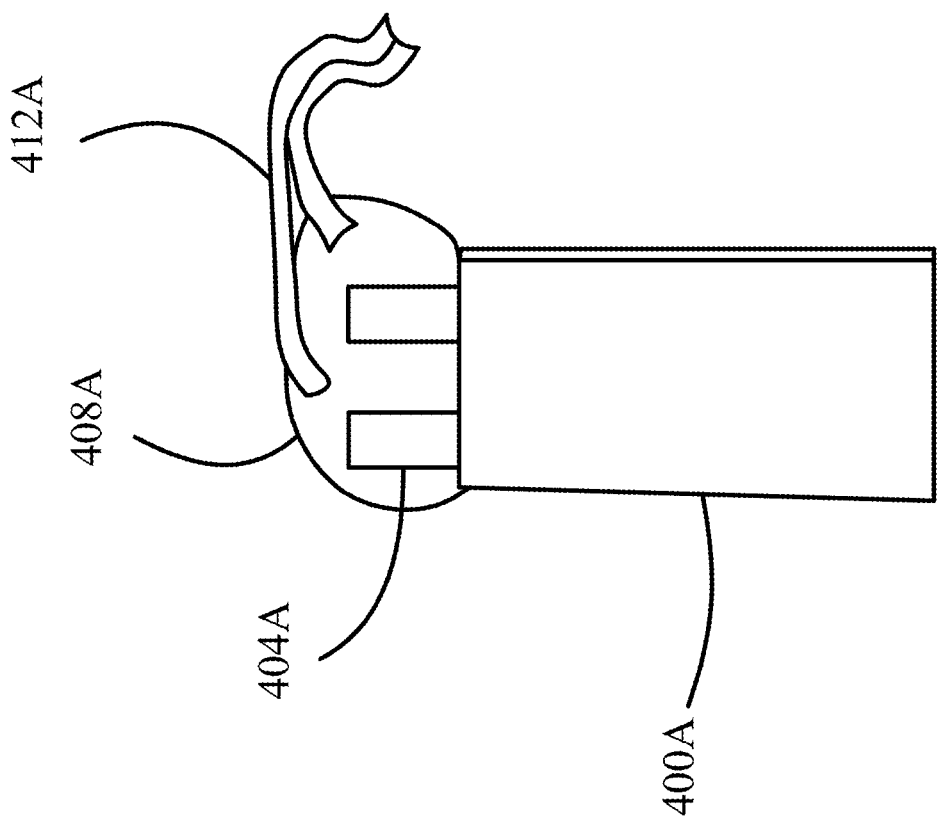
FIG. 4B
FIG. 4A

SYSTEM AND METHOD FOR A WEARABLE CIRCUIT

CROSS-REFERENCE TO RELATED APPLICATIONS

This application claims the benefit of priority of U.S. Provisional Patent Application Ser. No. 63/050,468, filed on Jul. 10, 2020, and titled "ADAPTIVE SOFT BATTERY APPARATUS AND METHODS OF MANUFACTURING AN ADAPTIVE SOFT BATTERY APPARATUS" of which is incorporated by reference herein in its entirety.

FIELD OF THE INVENTION

The present invention generally relates to the field of electronics. In particular, the present invention is directed to a wearable circuit system and methods of manufacturing the same.

BACKGROUND

Current battery packs are bulky and rigid, and frequently encased in hard plastics. Commonly, hard casing and bulky nature of these battery packs makes them difficult to incorporate into wearable devices, where extra comfort and flexibility is needed. In addition, current battery packs are difficult to conform to a variety of flat and curved body surfaces.

SUMMARY OF THE DISCLOSURE

In an aspect, a system for a wearable circuit is described. The system includes a soft substrate. The system include a first battery assembly attached to the soft substrate. The system includes a second battery assembly attached to the soft substrate. The system includes a flexible connecting device. A flexible connecting device is configured to connect a first battery assembly to a second battery assembly and stretch along a path of a soft substrate. A flexible connecting device provides an electrical connection between a first and second battery assembly while being stretched.

In an aspect, a method of fabricating a wearable circuit. The method includes selecting a soft substrate. The method includes selecting a first battery assembly and a second battery assembly. The method includes selecting a flexible connecting device. The flexible connecting device is configured to provide an electrical connection between a first battery assembly and a second battery assembly. The flexible connecting device is configured to stretch along a path of a soft substrate. The method includes connecting a first battery assembly to a second battery via a flexible connecting device. The method includes attaching a first battery assembly, a second battery assembly, and a flexible connecting device to a soft substrate.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 2A-C illustrate particular embodiments of a wearable circuit system;

FIGS. 4A-4F illustrate various embodiments of a wearable circuit system;

Figure 1A:
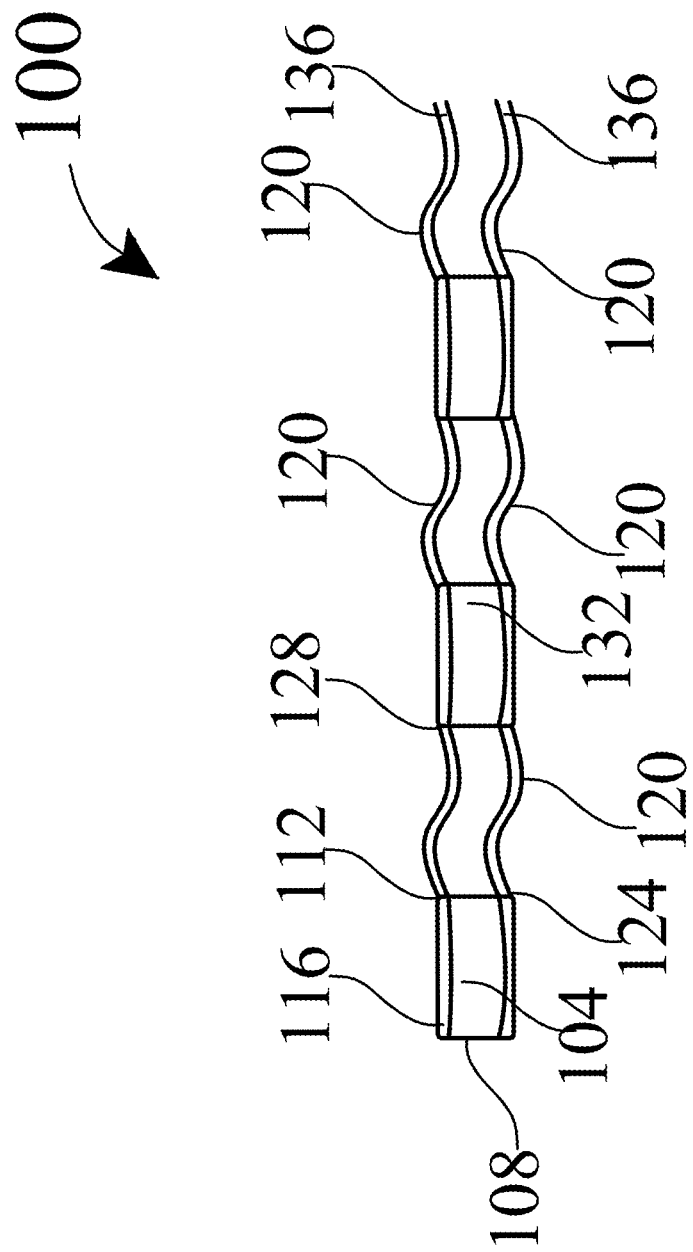
FIGS. 1A-1B are diagrammatic representation of a wearable circuit system.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to a system for a wearable circuit and methods of manufacturing a wearable circuit. A wearable circuit allows for customization of battery voltages and current capacities, to be incorporated into a variety of various textiles, or other comfortable materials, that may have varying electrical requirements. In addition, the soft substrate and flexible nature of the flexible connecting device of the wearable circuit allows the wearable circuit to conform to various shape and size requirements. The wearable circuit is suitable to be incorporated into clothing, smart devices, furniture, and other gadgets.

In one embodiment, a system for a wearable circuit is presented. The system may include a soft substrate. In some embodiments, a soft substrate may include a fabric. In some embodiments, a soft substrate may include a bra. The system may include a first battery assembly. A first battery assembly may be configured to attach to a soft substrate. A first battery assembly may be configured to house a flexible connecting device. A first battery assembly may be configured to include a mechanical battery holder. The system may include a second battery assembly. A second battery assembly may be configured to attach to a soft substrate. In some embodiments, a first and second battery assembly may be configured to be in a stacked arrangement. The system may include a flexible connecting device. A flexible connecting device may be configured to provide an electrical connection between a first and second battery assembly while being stretched. In some embodiments, a flexible connecting device may be configured to compress along a path of a soft substrate. In some embodiments, a flexible connecting device may include a conductive core material surrounded by an insulating outer layer. In some embodiments, a flexible connecting device may be configured to provide multiple electrical connections to a plurality of battery assemblies.

In one embodiment, a method of fabricating a wearable circuit is presented. The method may include selecting a soft substrate. A soft substrate may include a fabric. A soft substrate may include a bra. The method may include selecting a first battery assembly and a second battery assembly. In some embodiments, a first battery assembly may be configured to house a flexible connecting device. In some embodiments, a first battery assembly may include a mechanical battery holder. The method may include selecting a flexible connecting device. A flexible connecting device may be configured to provide an electrical connection between a first battery assembly and a second battery assembly. A flexible connecting device may be configured to stretch along a path of a soft substrate. A flexible connecting device may be configured to compress along a path of a soft substrate. In some embodiments, a flexible connecting device may be configured to provide multiple connections to a plurality of battery assemblies. In some embodiments, a flexible connecting device may include a printed circuit board. The method may include connecting a first battery assembly to a second battery assembly via a flexible connecting device. The method may include attaching a first battery assembly, a second battery assembly, and a flexible connecting device to a soft substrate. In some embodiments, a first battery assembly, a second battery assembly, and a flexible connecting device may be configured to be encapsulated in a soft substrate.

Referring now to FIG. 1A, an exemplary embodiment of a wearable circuit 100 is illustrated. In some embodiments, wearable circuit 100 may include a first battery assembly 104. First battery assembly 104 may be configured to attach to a soft substrate. In some embodiments, first battery assembly 104 may be configured to be encapsulated into a soft substrate. In some embodiments, first battery assembly 104 may include a first end 108 and a second end 112. In some embodiments, first battery assembly 104 may include at least a battery cell; in some embodiments, first battery assembly may include a plurality of battery cells. A "battery cell," as used in this disclosure, is a device containing one or more electrochemical cells with an external connection. An electrochemical cell includes any device capable of generating electrical energy from a chemical reaction and/or using electrical energy to cause a chemical reaction. A battery cell may include a coin battery, a cylinder battery, a primary battery, a secondary battery, a wet cell battery, a dry cell battery, a molten salt battery, a reserve battery, a rechargeable battery, and the like. A battery cell may accommodate various capacity electric charges, to deliver various rated voltage, including for example satisfying various voltage, capacity and/or discharge current requirements. In a non-limiting example, a battery cell may supply power at 1.5V. In yet another non-limiting example, a battery cell may supply power at 3V or 9V. A battery cell may include a container, configured to house components of a battery cell. A battery cell may contain a separator, including a non-woven fibrous fabric that separates electrodes. A battery cell may contain an electrolyte, containing a medium that causes the movement of ions within the battery cell. A battery cell may contain an anode electrode through which electrons are discharged, and a cathode electrode through which electrons are charged. A battery cell may contain a collector, containing a pin such as a brass pin that conducts electricity to an outside circuit.

With continued reference to FIG. 1A, a first battery assembly 104 may be configured to be encapsulated into a soft substrate. A "soft substrate," as used in this disclosure, is a material that is easy to mold and shape and is not firm to the touch. A soft substrate may include but is not limited to rubber, silicone, woven fiber, polymers, granular materials and/or foam. A soft substrate may include a washable material. A "washable material," as used in this disclosure, is any material capable of being washed without damage. Washing may include using a washing machine, including any home appliance used to wash laundry. Washing may include hand-washing, including washing an item by hand, without the use of a washing machine. Washing may include utilizing one or more ingredients such as water, soap, detergent, stain remover, fabric softener, cleanser, castile, and the like during the washing process. A soft substrate may include a flexible material, capable of being modified to respond to altered circumstances and/or altered conditions. A soft substrate may include a waterproof material that is impervious to liquids, such as water. A soft substrate may allow wearable circuit system 100 to be integrated into textiles and/or garments. A flexible material may include a material that may be integrated into various size garments and/or textiles, and may be capable of bending, twisting, and/or stretching. For example, a flexible material may be capable of being integrated into a first textile such as a sock, and a second textile such as a bra. A flexible material may be easily bent and is subject to modification and/or adaptation. A soft substrate may allow integration of a wearable circuit into various fabrics and/or textiles, including but not limited to underwear, bras, t-shirt, shorts, socks, pants, shoes, hats, dresses, skirts, handbags, wallets, and the like. A soft substrate may allow integration of a wearable circuit into various gadgets, items of furniture, and/or electronics such as but not limited to a watch, car interior, rug, chair, blanket, sheet, pillow, and/or any other apparatus that aims to require a flexible and versatile way to incorporate a wearable circuit system into various items. A soft substrate may include multiple layers, where each layer may be composed of one or more materials, including any of the materials as described above. In an embodiment, each layer may include a varying thickness.

With continued reference to FIG. 1A, wearable circuit system 100 may include a first battery holder 116. A "battery holder," as used in this disclosure, is any compartment configured to interface with a battery assembly. A battery holder 116 may interface with a battery cell. In some embodiments, battery holder 116 may interface with a battery cell of a battery holder 116 that may hold and/or surround a battery cell. A battery holder 116 may interface with a battery cell, by making electrical contact with the battery cell. A battery holder 116 may surround a first end 108 and a second end 112 of a first battery assembly 104. A battery holder 116 may include a mechanical battery holder. A mechanical battery holder may include a rigid structure that may be configured to house a battery assembly 104. In some embodiments, a mechanical battery hold may be configured to hold battery assembly 104 in a fixed position. In some embodiments, a mechanical battery holder may include an insulated structure and a conductive element, the conductive element in contact with a first battery assembly 104. An insulated structure may be composed of a plastic material and may include a shape that may be molded to create a compartment that may accept a first battery assembly 104 and completely surround first battery assembly 104. A mechanical battery holder may include a lid that may retain and protect a first battery assembly 104. A mechanical battery holder may be configured to prevent damage to circuitry and/or components from any battery cell leakage. A conductive element may include one or more metallic or non-metallic elements, that may aid in electrical conduction. A conductive element may include but is not limited to, lead, zinc, copper, carbon, cadmium, nickel oxide hydroxide, iron, manganese dioxide, vanadium, lithium, sodium, lithium iron phosphate, nickel cobalt aluminum oxide, lithium manganese oxide, lithium titanite, nickel manganese cobalt oxide, lithium sulfur, and/or zinc bromine. A battery holder may include an opening configured to house a flexible connecting device. An opening may include a hole and/or slot configured to house a flexible connecting device. In an embodiment, an opening may be of a diameter configured to encompass and/or surround a flexible connecting device. A battery holder may be configured to house flexible connecting device 120 by providing a containing structure that may be configured to contain flexible connecting device 120. In some embodiments, a battery holder may be configured to house an end of flexible connecting device 120. In some embodiments, a battery holder may be configured to house an entirety of flexible connecting device 120. In an embodiment, a mechanical battery holder may include a printed circuit board, including but not limited to a flexible printed circuit board, a rigid printed circuit board, and/or a rigid-flexible printed circuit board. In an embodiment, a battery holder 116 may interface with a flexible connecting device 120 using a solder joint, solder bond, physical joint, chemical joint, mechanical joint, and the like.

With continued reference to FIG. 1, a battery holder 116 may include a magnetic battery holder configured to connect to a positive electrode located on a battery cell and a negative electrode located on the battery cell. An "electrode" as used in this disclosure is an electrical conductor used to make contact with a nonmetallic part of a circuit. An electrode may include, but is not limited to, a gas electrode, a metal salt electrode, a metal ion electrode, and/or a redox electrode. A magnetic battery holder may contain a material such as iron, ore, alloy, and/or any other material that produces a magnetic field. In an embodiment, a magnetic battery holder may include an opening, including any of the openings as described above in more detail. An opening located within magnetic battery holder may be configured to house a flexible connecting device 120.

With continued reference to FIG. 1A, a battery holder may include a printed circuit board that may include a flexible connecting device. A configured to attach to a first battery assembly 104. A "printed circuit board," as used in this disclosure, is a board that mechanically supports and electrically connects electronic components using conductive tracks, pads, and other features etched from one or more sheet layers of a conductive element onto/and or between sheet layers of a non-conductive element. A printed circuit board mechanically supports and electrically connects electric components using conductive tracks and other features. Components may be soldered onto a printed circuit board to electrically connect and mechanically fasten them to it. A printed circuit board may include a single-sided circuit board, a double-sided circuit board, and/or a multi-layer circuit board. A printed circuit board may include a flexible printed circuit board, a rigid printed circuit board, and/or a rigid-flexible printed circuit board.

With continued reference to FIG. 1A, wearable circuit system 100 may include a flexible connecting device 120. A "flexible connecting device," as used in this disclosure, is a conductive element that provides an electrical connection between two objects and is configured to stretch, compress, shape, contort, twist, bend, or otherwise align itself to a shape of a soft substrate. A flexible connecting device 120 may include a first wire end 124 and a second wire end 128. A first wire end 124 may be configured to attach to a first battery assembly 104 and a first battery holder 116. A second wire end 128 may be configured to attach to a second battery assembly 132, which may include anything suitable for use as first battery assembly as described above, and a second battery holder. In an embodiment, a first wire end 124 and/or a second wire end 128 may include two terminals. The two terminals may be configured to connect a first battery assembly 104 to a second battery assembly 132, and/or another component. A flexible connecting device 120 may include a cylindrical, flexible rod shape. A flexible connecting device 120 may include any electrically conductive element configured to connect a first battery assembly 104 with a first wire end 124. In some embodiments, a first wire end 124 may be configured to be located on a flexible connecting device 120. A flexible connecting device 120 may include but is not limited to a wire, a printed circuit board including, a flexible printed circuit board, a rigid printed circuit board, a flexible-rigid printed circuit board, a flat cable, a conductive thread, and the like. A "conductive element," as used in this disclosure, is an object and/or material that allows the flow of electrical current and/or charge in one or more directions. Electrical current may be generated by the flow of negatively charged electrons, positively charged holes, and/or positive or negative ions. An electrically conductive element may include one or more materials including metals, electrolytes, superconductors, semiconductors, plasma, and/or nonmetallic materials such as graphite and/or conductive polymers. For instance and without limitation, an electrically conductive element may include but is not limited to, copper, silver, aluminum, oil, platinum, silver, iron, copper, gold, and the like. A flexible connecting device 120 may include a thermoplastic-sheathed cable (TPS) and/or nonmetallic cable such as ROMEX™ as produced by Southwire Company, LLC of Carrollton Georgia. A flexible connecting device 120 may be configured to be insulated by an individual thermoplastic sheath with a particular exterior color used to indicate the purpose of the conductor. A non-metallic cable may include a cable that may include an exterior outer sheathing that may not be metallic. In an embodiment, a conductive shield may surround conductive material of the cable. A conductive shield may include for example, a Hochstadt shield. A cable may include a twisted pair, extensible, coaxial, shielded, and/or communication cable.

With continued reference to FIG. 1A, a flexible connecting device 120 may include an electrically conductive core material, surrounded by an insulating outer layer. An electrically conductive core material includes any material suitable for use as an electrically conductive element as described above in more detail. An electrically conductive core may include material at a central location of a flexible connecting device 120. An electrically conductive core may include a single, cylindrical, and/or flexible strand or rod containing an electrically conductive element. An electrically conductive core may include a plurality of filament conductors. Filament conductors may include two or more strands wrapped and/or bundled together to form a larger conductive element. One or more strands may be woven together and/or braided together loosely and/or optionally combined with an elastic, and/or any material that may enable the strands to retain elasticity. For instance and without limitation, an electrically conductive core may include seven strands of wire, containing one in the middle with six wires surrounding the middle wire, all in close contact. Filament conductors may be fused together, such as for example, perfused wire. Filament conductors may be braided together, containing wires that are braided into one larger conductive element. An electrically conductive core may be surrounded by an insulating outer layer. An "insulating outer layer," as used in this material, is any material that surrounds and/or encompass an electrically conductive core. An insulating outer lay may include a material that has low electrical connectivity. An insulating outer layer may be composed of one or more materials such as plastic, including for example, polyethylene, and/or polyurethane. In an embodiment, flexible connecting device 120 may be configured to act as a battery holder. For example, flexible connecting device 120 may connect directly to a first battery assembly 104 in lieu of a mechanical battery element. A second electrically conductive element may be used to transition in a connection between a flat surface located on a battery cell to a cylindrical surface located on a flexible connecting device 120. A second electrically conductive element may include any electrically conductive material as described herein. In an embodiment, a flexible connecting device 120 may include a flexible printed circuit board, and/or a conductive textile. In yet another non-limiting example, a flexible connecting device 120 may include a wire containing one or more flexible printed circuit board connectors. In an embodiment, wearable circuit system 100 may include a plurality of flexible connecting devices 120 that may create a series connection of battery cells. In an embodiment, wearable circuit system 100 may include a plurality of flexible connecting devices 120 that may create a parallel connection of battery cells. Flexible connecting device 120 may allow for a plurality of battery cells to be configured in varying placements and/or connections to accommodate power requirements and/or geometrical shapes of various textiles that may comfortably accommodate wearable circuit 100. Flexible connecting device 120 may allow for wearable circuit 100 to configure to varying geometries of a human body when incorporated into a garment. Flexible connecting device 120 may allow for one or more battery cells contained within wear 100 to be stretched and/or compressed to accommodate varying angles, textiles, garments, and/or placements on a human body.

In some embodiments, and with continued reference to FIG. 1A, flexible connecting device 120 may be configured to be flexible. As used in this disclosure, "flexible" is defined as being capable of elongation through elastic deformation and producing a recoil force that urges the flexible material to resume a former shape or size. In some embodiments, an elastic material may include, but is not limited to, natural gum, spandex, fluoroelastomer, elastomer, ethylene-propylene rubber, resilin, styrene-butadiene rubber, chloroprene, elastin, rubber epichlorohydrin, and/or nylon. In some embodiments, flexible connecting device 120 may be configured to provide an electrical communication between battery assemblies while stretched. Flexible connecting device 120 may be configured to conduct electricity when in a resting position. In some embodiments, flexible connecting device 120 may be configured to conduct electricity while in the process of elongation through elastic deformation. In some embodiments, flexible connecting device 120 may be configured to conduct electricity once elongated through stretching. In some embodiments, flexible connecting device 120 may be configured to conduct electricity while in the process of resuming a former shape and/or size. Flexible connecting device 120 may be configured to conduct electricity in any position or combination thereof as described above.

With continued reference to FIG. 1A, a flexible connecting device 120 may include a power transmission wire. A "power transmission wire," as used in this disclosure, is a wire involved in the movement of electrical energy. A power transmission wire may include one or more hot wires, ground wires, neutral wires, and/or communication wires. A flexible connecting device 120 may include a communication wire. A "communication wire," as used in this disclosure, is a wire that sends and/or receives computer data, television and sound wire, telemechanical data, telephone data, photograph data, sensor data, and the like. A communication wire may include transmission media that includes optical fiber, coaxial conductors, copper conductors, and/or twisted wire pairs. Communication wires may include wires that may be utilized to control devices, including for example, medical devices, sensors, appliances, and the like. Communication wires may include wires that connect with the internet and may be part of the internet of things. In an embodiment, a communication wire may be located on a printed circuit board and interface with a battery assembly.

With continued reference to FIG. 1A, second wire end 128 may include a terminal end 136. Terminal end 136 may exit a wearable circuit. In an embodiment, a terminal end 136 may include a positive wire terminal and a negative wire terminal. Additional wires may also exit at terminal end 136, such as for example, a data wire. In some embodiments, a data wire may be configured to provide battery capacity. In an embodiment, a terminal end 136 may exit an nth battery holder. For example, in an embodiment, wearable circuit system 100 may include five battery holders connected together by a flexible connecting device 120. In such an instance, a terminal end 136 may exit a fifth battery holder. In some embodiments, terminal end 136 may be configured to extend an electrical connection to an exterior component. In some embodiments, an exterior component may include an external computing device. In some embodiments, an exterior component may include an external power source. In an embodiment, wearable circuit system 100 may include eight battery holders connected together by flexible connecting device 120. In such an instance, a terminal end 136 may exist an eighth battery holder. One or more battery cells contained within wearable circuit system 100 may be configured to include a stacked arrangement. A stacked arrangement may include an arrangement in which two or more battery assemblies may be physically positioned on top of one another. In some embodiments, a stacked arrangement may include a column and row. In some embodiments, a stacked arrangement may include a plurality of columns and rows. A stacked arrangement may be configured to place battery assemblies in a series connection to create higher voltage. In some embodiments, a stacked arrangement may be configured to place battery assemblies in a parallel connection to create a higher current capacity.

With continued reference to FIG. 1A, wearable circuit system 100 may include a safety circuit. A safety circuit may include a device that prevents malfunction of wearable circuit system 100 such as by sounding an alert and/or activating the safety circuit if there is a malfunction. In an embodiment, a safety circuit may include an additional battery cell that protects a first battery assembly 104 and/or any other component of wearable circuit system 100. In an embodiment, a safety circuit may be located adjacent to a first battery assembly 104 or located in between a first battery assembly 104 and a first battery holder 116. Wearable circuit system 100 may be configured to accept various dimensions and various electrical requirements in a first battery assembly 104 such as various voltages and/or various discharge currents, that may allow wearable circuit system 100 to be adapted in various textiles and/or garments that may have various voltages and/or discharge current requirements.

With continued reference to FIG. 1A, wearable circuit system 100 may include an attachment. An "attachment," as used in this disclosure, is any device that aids in attaching a wearable circuit to a textile. An attachment may include for example, a wire, snap, opening, groove, fastener, hook, indentation, pin, and the like. An attachment may allow wearable circuit system 100 to be attached to a textile and/or conduct power through the textile. A textile may include a garment worn proximately to the body and may contact the body in one or more locations. A textile may include intimate apparel including but not limited to, a bra, underwear, sports bra, bralette, mastectomy bra, brassier, nursing bra, strapless bra, balconette bra, t-shirt bra, racerback bra, wireless bra, stick on bra, push up bra, unlined bra, maternity bra, bandeau bra, longline bra, halter bra, plunge bra, demi bra, full coverage bra, padded bra, underwire bra, convertible bra, pantyhose, swimwear, underwear, body shapeware, thong, corset, pajamas, boxer shorts, briefs, knickers, t-shirt, sleeveless shirts, singlets, tank tops, camisole, basque, bodice torsolette, and the like. A bra may include a supportive garment that may provide support to human mammary glands. A textile may include for example an item of clothing such as a shirt, pant, hat, underwear, bra, headband, skirt, dress, socks, jumpsuit, sleepwear, swimwear, exercise clothes, and the like. A textile may include an appliance such as a watch, car interior, rug, chair, and/or any item containing textiles.

In some embodiments, and with continued reference to FIG. 1A, an attachment may include a mechanical power switch. A mechanical power switch may be configured to turn wearable circuit system 100 on or off. A mechanical power switch may include an electrical component that operates to connect and/or disconnect a conducting path of electric current in a wearable circuit system 100. A mechanical power switch may include one or more sets of moveable electrical contacts connected to external circuits. When electrical contacts touch, electrical current can pass between them, while when electrical contacts are separated, electrical current cannot pass between them. An electrical contact may include a conductive element, including any material suitable for use as electrically conductive element as described above. A mechanical power switch may be operated manually. In an embodiment, a mechanical power switch may be located within wearable circuit system 100. In an embodiment, a mechanical power switch may be located external to a wearable circuit system 100.

Figure 1B:
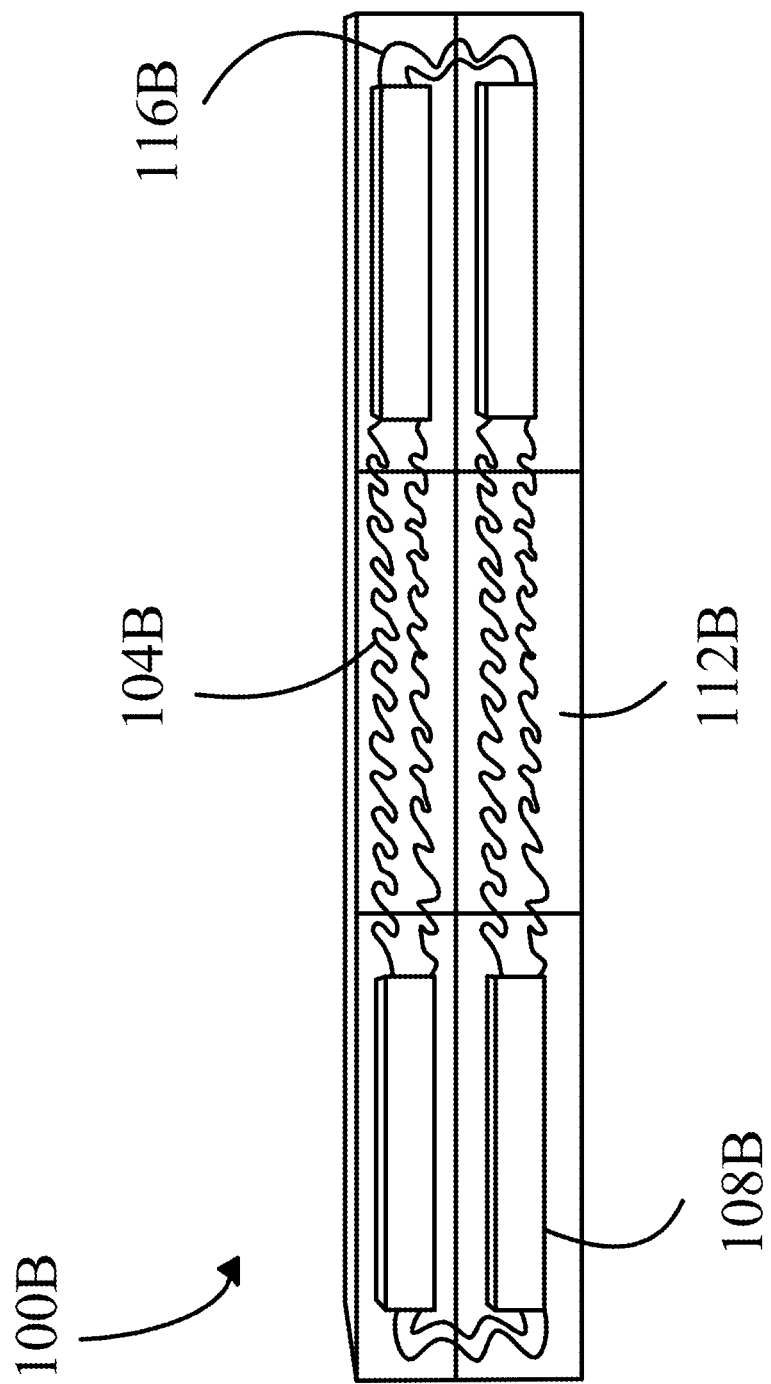

Referring now to FIG. 1B, an exemplary embodiment of a battery cell configuration of a wearable circuit system 100B is illustrated. In some embodiments, wearable circuit system 100B may include battery assembly 108B. Battery assembly 108B may include battery packs, battery cells and/or one or more electronic modules. Battery assembly 108B may be configured to store power in the form of electrical energy. In some embodiments, battery assembly 108B may be configured to deliver power to a component. In some embodiments, wearable circuit system 100B may include two or more battery assemblies 108B. In some embodiments, wearable circuit system 100B may include four battery assemblies 108B. Each battery assembly 108B of wearable circuit system 100B may be configured to have an electrical connection between one another. In some embodiments, two or more battery assemblies 108B may be configured to be in a series connection. In another embodiment, two or more battery assemblies 108B may be configured to be in a parallel. Connect. In one embodiment, battery assemblies 108B may be configured to include an arrangement. An arrangement may include a stacking arrangement in which two or more battery assemblies 108B may be stacked on top of one another. A stacking arrangement may include two columns of battery assemblies 108B. In some embodiments, a stacking arrangement may include more than two columns of battery assemblies 108B. In some embodiments, a stacking arrangement may include a row of battery assemblies 108B. In other embodiments, a stacking arrangement may include two or more rows of battery assemblies 108B.

With continued reference to FIG. 1B, in some embodiments, wearable circuit system 100B may include flexible connecting devices 104B. Flexible connecting devices 104B may be configured to connect two or more battery assemblies 108B. In some embodiments, flexible connecting devices 104B may be configured to provide an electrical connection between two or more battery assemblies 108B. In some embodiments, flexible connecting devices 104B may be configured to communicate data between two or more battery assemblies 108B. In some embodiments, flexible connecting devices 104B may be configured to extend, compress, twist, curve, bend, or otherwise conform to a shape of substrate 112B. In some embodiments, wearable circuit system 100B may include interconnections 116B. Interconnections 11B may be configured to connect two or more batteries on a same side of substrate 112B. In some embodiments, interconnections 108B may be configured to vertically compress and stretch. In some embodiments, interconnections 108B may be configured to horizontally compress and stretch. Interconnections 108B may be configured to transmit power, data, or other electrical signals between two or more battery assemblies 108B. In some embodiments, substrate 112B may include rubber, silicone, woven fiber, polymers, granular materials and/or foam. In some embodiments, battery assemblies 108B may be configured to be partially attached to substrate 104B. In some embodiments, battery assemblies 108B may be configured to be fully attached to substrate 104B. In some embodiments, battery assemblies 108B may be configured to be encapsulated in substrate 104B. In some embodiments, flexible connecting devices 104B and interconnections 116B may be configured to be partially attached to substrate 112B. In some embodiments, flexible connecting devices 104B and interconnections 116B may be configured to fully attach to substrate 112B. In some embodiments, flexible connecting devices 104B and interconnections 116B may be configured to be encapsulated by substrate 112B.

Figure 2C:
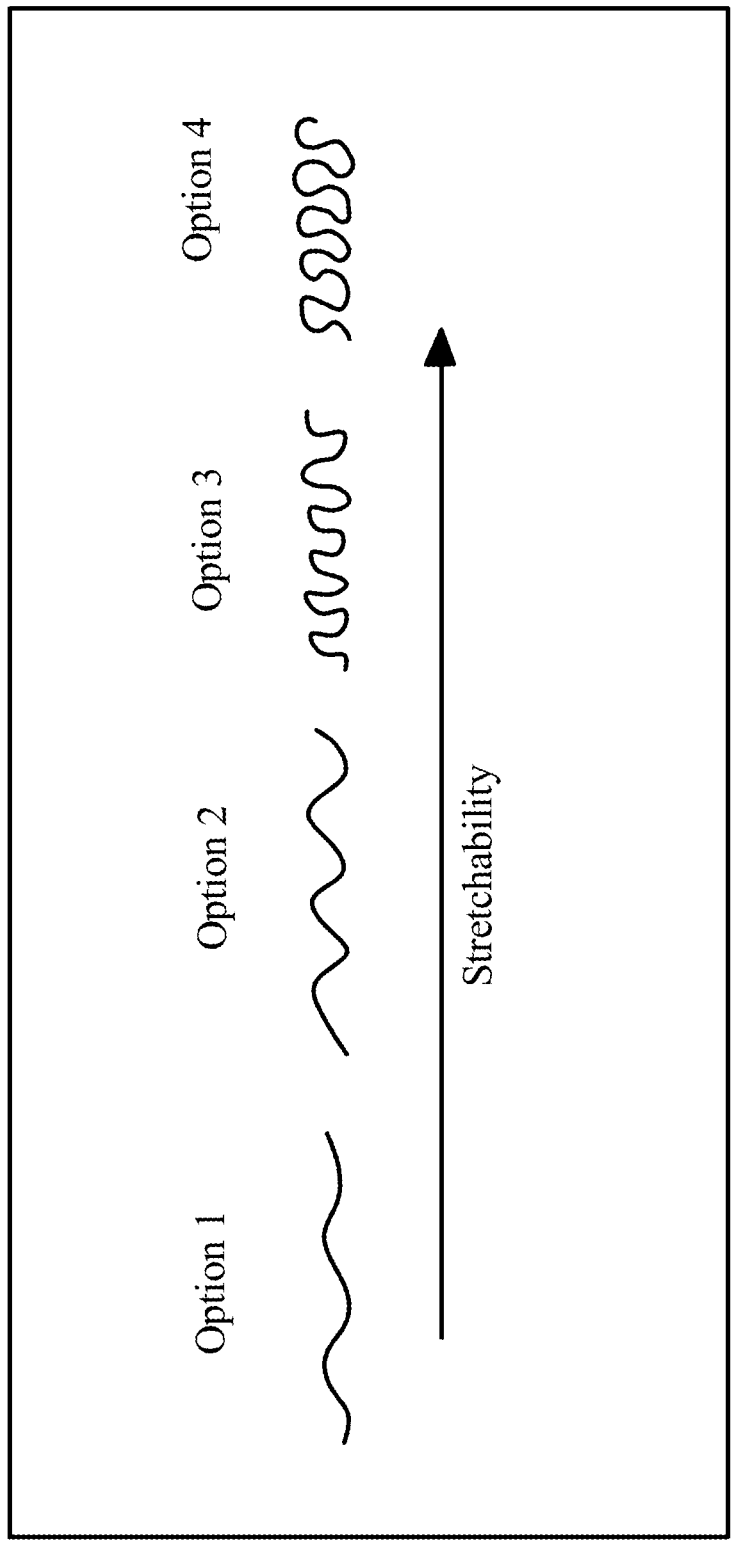

Referring now to FIGS. 2A-2C, exemplary embodiments of various configurations of a wearable circuit system 200 are illustrated. Referring first to FIG. 2A, in an embodiment, wearable circuit system 200 may include various quantities of battery cells, battery holders, and/or flexible interconnectors. In an embodiment, wearable circuit system 200 may include six battery cells, where each of the six battery cells are each surrounded by an individual battery holder. For example, wearable circuit system 200 may include a first battery assembly 204, a second battery assembly 232, a third battery assembly 204, a fourth battery assembly 208, a fifth battery assembly 212, and a sixth battery assembly 216. Each of the six battery cells may be each surrounded by an individual battery holder may be connected by a flexible connecting device 220, including any of the flexible connecting devices as described above in more detail in reference to FIG. 1A. In an embodiment, each of the six battery cells may be rigid. In an embodiment, each of the six battery cells may be flexible. In an embodiment, each of the six battery cells may be a combination of rigid and/or flexible. In an embodiment, each of the six battery cells may accommodate a varying electrical charge.

Referring now to FIG. 2B, in an embodiment, wearable circuit system may include two battery cells, where each of the two battery cells may be each surrounded by an individual battery holder. Each of the two battery cells each surrounded by an individual battery holder may be connected by a flexible connecting device 220, including any of the flexible connecting devices as described above in more detail in reference to FIG. 1A. For example, wearable circuit system 200 may include first battery assembly 204 and second battery assembly 232. In an embodiment, wearable circuit system 200 may include various quantities of battery cells, battery holders, and/or flexible interconnectors, based on factors such as what textiles, materials, and/or devices that wearable circuit system may be incorporated into.

Referring now to FIG. 2C, in an embodiment, varying degrees of stretchability of flexible connecting devices are illustrated. In an embodiment, option 1 shows flexible connecting devices configured to be more rigid. In option 1, flexible connecting devices may provide structural support to a substrate. Flexible connecting device of option 1 may be configured to resist a change in shape from an exterior force acting upon the flexible connecting device. In some embodiments, option 1 may be configured to be implemented in more rigid substrates, such as hard rubber. In some embodiments, a flexible connecting device may be configured to have a stretchability as shown in option 2. A flexible connecting device in option 2 may be configured to stretch slightly while retaining a somewhat rigid structure. In some embodiments, a flexible connecting device of option 2 may be configured in use of softer substrates. In some embodiments, a flexible connecting device may be configured to include a stretchability as shown in option 3. A flexible connecting device including a stretchability as shown in option 3 may be configured to stretch a large amount from a resting position. In some embodiments, a flexible connecting device of option 3 may be configured to provide slight resistance to exterior forces. In some embodiments, a flexible connecting device of option 3 may be implemented in substrates such as fabrics. In some embodiments, a flexible connecting device may be configured to have a stretchability as shown in option 4. A flexible connecting device of option 4 may be configured to have an extreme stretchability. A flexible connecting device of option 4 may be configured to stretch a great distance from a resting position. In some embodiments, a flexible connecting device of option 4 may be configured to be implemented in very soft substrates with a flexible structure. In some embodiments, flexible connecting device 120 may include a plurality of options between options 1, 2, 3 and 4. In a non-limiting example, a flexible connecting device may be configured to have a stretchability between option 1 and option 2. A flexible connecting device may have a stretchability based on a material used in the flexible connecting device. In some embodiments, flexible connecting devices 120 may include 5 or more options. In some embodiments, the options may be configured bas on a type of substrate that may be implemented into a wearable circuit system.

Figure 3:
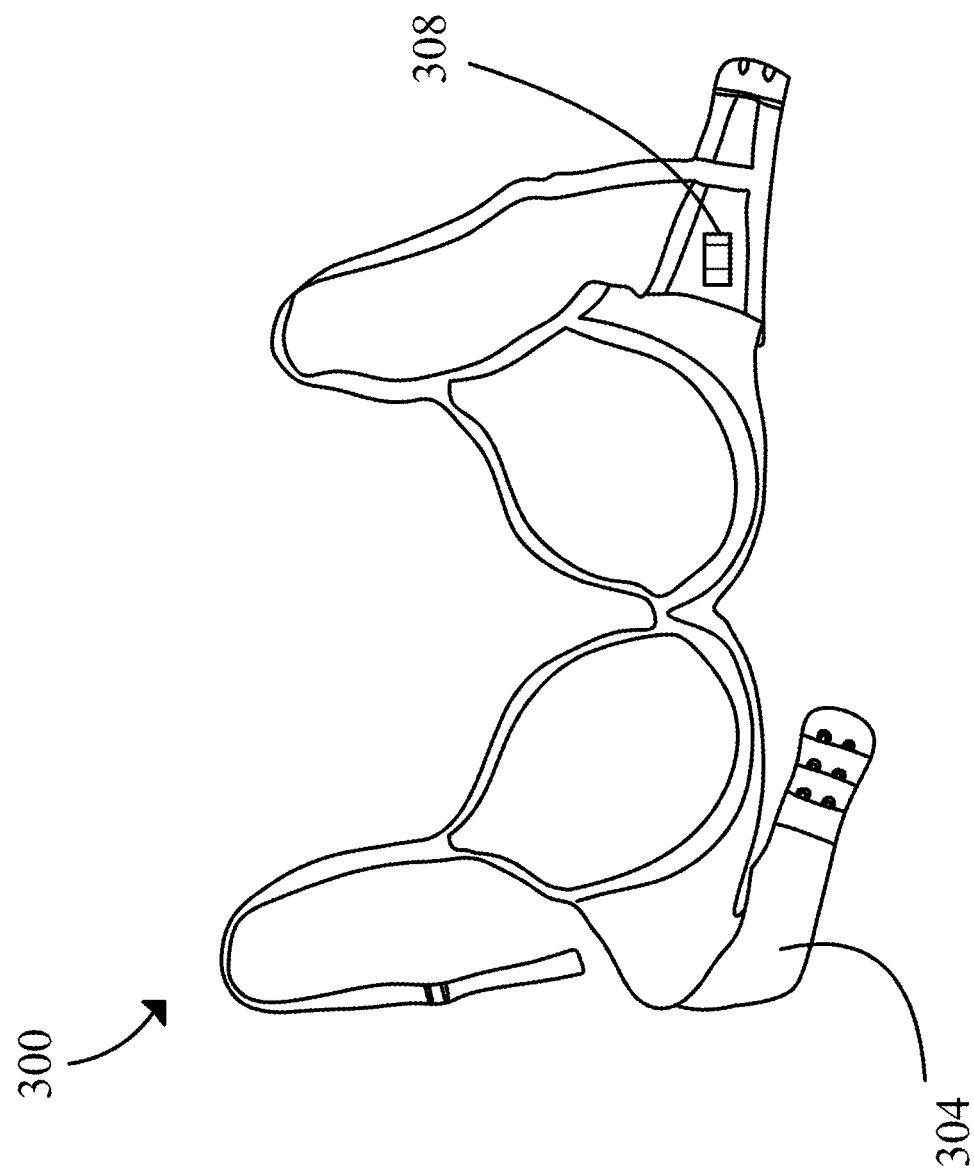
FIG. 3 is a diagrammatic representation of wearable circuit incorporated into a textile.

Referring now to FIG. 3, an exemplary embodiment 300 of wearable circuit system 308 incorporated into a textile 304 is illustrated. Wearable circuit system 308 may be incorporated into any textile and/or device, as described above in more detail in reference to FIG. 1A. In some embodiments, a plurality of wearable circuit systems 308 may be incorporated into a textile 304. In some embodiments, wearable circuit system 308 may be incorporated into a location of textile 304 that may prevent a user from feeling wearable circuit system 308 in textile 304. Wearable circuit system 308 may include a plurality of battery assemblies. In a non-limiting example, wearable circuit system 308 may include 40 battery assemblies. In some embodiments, wearable circuit system 300 may include less than or greater than 40 battery assemblies. In some embodiments, battery assemblies may include a battery cell. Each battery assembly may be surrounded by a battery holder. In some embodiments, each battery assembly may be surrounded by textile 304 without a battery holder. In some embodiments, each battery assembly may be connected by flexible connecting devices. Flexible connecting devices and battery assemblies may be embedded into textile 304. Textile 304 may include a brassier. In some embodiments, textile 304 may include a washable material. A washable material may include a fabric that may be configured to withstand a washing process, such as but not limited to, a machine-washing cycle. In an embodiment, flexible and/or twistable qualities of flexible connecting devices may allow for wearable circuit system to be compactly integrated into various textiles. Flexible and/or twistable qualities of flexible connecting devices as described above in more detail may also allow wearable circuit system 308 to be incorporated into textiles and/or devices of various sizes and shapes, based on flexible, bendable, and flexible nature of the flexible connecting devices, that may allow wearable circuit system 308 to be expanded and/or contracted as needed. In some embodiments, wearable circuit system 308 may include a breathable material. A "breathable material" as used in this disclosure is a material that easily allows gases and/or vapors to pass through a surface of the material. A breathable material may include, but is not limited to, cotton, nylon, polyester, rayon, linen, silk, merino wool, or other breathable materials. In an embodiment, wearable circuit system 308 may be incorporated into textile 304 using an attachment, as described above in more detail in reference to FIG. 1A. In such an instance, multiple battery assemblies may be interconnected to one another and incorporated into textile 304 such as a bra. Multiple battery assemblies may be interconnected to one another using one or more flexible connecting devices in a parallel connection to maximize current capacity. Multiple battery cells may be interconnected to one another using one or more flexible connecting devices in a series connection.

In some embodiments, and with continued reference to FIG. 3, wearable circuit system 308 may be configured to include a sensor. A sensor may be configured to measure a heartbeat, temperature, electrocardiogram (EKG), motion, respiratory rate, ultrasound, and/or other data. In some embodiments, a sensor may attach separately to textile 304. In some embodiments, a sensor may be configured to be incorporated into textile 304 with wearable circuit system 308. In some embodiments, wearable circuit system 308 may include a database. A database may include a storage and/or memory device. In some embodiments, a database may include an external computing system configured to receive sensory information from wearable circuit system 308. In some embodiments, wearable circuit system 308 may be configured to wirelessly transmit data to and from an external computing device. In some embodiments, wearable circuit system 308 may be configured to communicate with a server. In some embodiments, wearable circuit system 308 may be configured to communicate with a smartphone, tablet, or other device. In some embodiments, wearable circuit system 308 may be configured to connect to an external computing device through a wired connection. In some embodiments, wearable circuit system 308 may include an NFC component. In some embodiments, wearable circuit system 308 may include an RFID component. In some embodiments, wearable circuit system 308 may include a GPS component. In some embodiments, wearable circuit system 308 may include a Bluetooth component. In some embodiments, wearable circuit system 308 may include a Wi-Fi component. Wearable circuit system 308 may be configured to communicate with nearby devices through the Internet of Things. In some embodiments, wearable circuit system 308 may be configured to send and/or display data to an external computing device of measured sensory data. In one embodiment, wearable circuit system 308 may connect to a smartphone via Bluetooth. In some embodiments, wearable circuit system 308 may be configured to display biological data of a user on a smartphone. In some embodiments, wearable circuit system 308 may be configured to display battery health, status, life, charge, and the like on a smartphone. In some embodiments, wearable circuit system 308 may be configured to display a trend of historical data measured on a smartphone. In some embodiments, wearable circuit system 308 may be configured to send a push notification to an external computing device, such as but not limited to, a smartphone. In some embodiments, wearable circuit system 308 may be configured to send data to an external computing device about a charge status, battery health, and/or remaining battery life of a battery assembly. In some embodiments, wearable circuit system 308 may be configured to send alerts to an external computing device. Alerts may include data about heart rate, blood pressure, temperature, motion, respiratory rates, heart rhythms, and/or other datum. In some embodiments, wearable circuit system 308 may be configured to receive data, instructions, and/or other communications from an external computing device. In some embodiments, an external computing device may be a computing device of a healthcare provider, such as a doctor. In some embodiments, wearable circuit system 308 may be configured to alert a healthcare provider of any irregularities regarding heart rate, respiratory rate, heart rhythm, and the like.

In some embodiments and with continued reference to FIG. 3, wearable circuit system 300 may be configured to receive power through a wireless charging component. A wireless charging component may include an induction charger. An induction charger may be configured to receive an alternating current (AC) and output a fluctuating magnetic field. A fluctuating magnetic field may interact with a magnetic component of wearable circuit system 308. A fluctuating magnetic field may induce an AC current in a magnetic component, which may transmit power. In some embodiments, wearable circuit system 308 may be configured to include a charging port. A charging port may be configured to extend to an exterior side of a fabric. In some embodiments, a charging port may be configured to convert alternating current (AC) to direct current (DC). In some embodiments, a charging port may be configured to receive USB, micro-USB, USB-C, or other charging standards. In some embodiments, a charging port may be configured to receive between 1 W to 10 W of power. In some embodiments, a charging port may be configured to receive greater than 10 W of power. In some embodiments, a charging port may include a fast charging device. A fast charging device may be configured to rapidly deliver power to a battery assembly of wearable circuit system 308. In some embodiments, wearable circuit system 308 may be configured to include a power capacity of 2,000 mAh. In some embodiments, wearable circuit system 308 may be configured to include a power capacity of greater than 2,000 mAh.

Figure 4C:
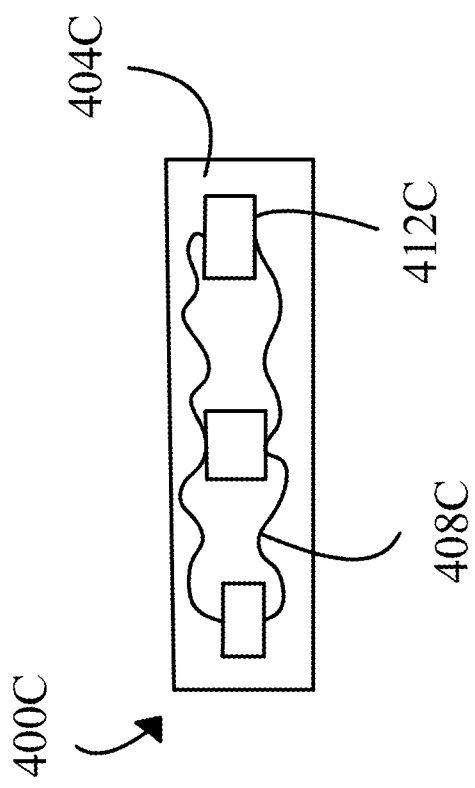

Referring now to FIGS. 4A-4E, various embodiments 400 of a wearable circuit system are illustrated. Referring to FIG. 4A, illustrates an example of a battery assembly 400A. Battery assembly 400A may be configured to not include a mechanical battery holder. In some embodiments, a flexible connecting device may be configured to function as a battery holder. A flexible connecting device may be configured to surround at least a portion of battery cell 400A. In some embodiments, a flexible connecting device may be configured to structurally support a battery assembly 400A. In some embodiments, battery assembly 400A may include solder joint 404A. Solder joint 404A may be configured to provide an electrical contact. In some embodiments, battery assembly 400A may include two or more solder joints 404A. In some embodiments, solder joints 404A may be configured to enable an electrical connection between battery assembly 404A and another object. In some embodiments, battery assembly 400A may include an encapsulation 408A. Encapsulation 408A may include a substrate. In some embodiments, encapsulation 408A may be configured to hold battery assembly 400A in a substrate. In some embodiments, a substrate may include a fabric. In some embodiments, battery assembly 400A may include cables 412A. Cables 412A may be configured to connect to solder joint 404A. In some embodiments, cables 412A may be configured to extend an electrical connection to battery assembly 400A. Cables 412A may include a conductive element. A conductive element may include but is not limited to, lead, zinc, copper, carbon, cadmium, nickel oxide hydroxide, iron, manganese dioxide, vanadium, lithium, sodium, lithium iron phosphate, nickel cobalt aluminum oxide, lithium manganese oxide, lithium titanite, nickel manganese cobalt oxide, lithium sulfur, and/or zinc bromine.

Referring now to FIG. 4B, an example of a battery assembly 400B including a mechanical battery holder 416B is illustrated. In some embodiments, mechanical battery holder 416B may include any material suitable for use as soft substrate, including any of the soft substrate materials as described above in more detail in reference to FIG. 1A. In an embodiment, mechanical battery holder 416B may include a hard material that may aid in mechanically protecting solder joint 404B when wearable circuit system is stretched. In an embodiment, mechanical battery holder 416B may include a combination of soft and/or hard materials. In some embodiments, solder joint 404B may be configured to provide an electrical contact of battery assembly 400B. In some embodiments, battery assembly 400B may include encapsulation 408B. Encapsulation 408B may include a substrate. A substrate may include a fabric. In some embodiments, encapsulation 408B may be configured to hold battery assembly 400B in a position of a substrate. In some embodiments, battery assembly 400B may include cables 412B. Cables 412B may be configured to connect to solder joint 404B. In some embodiments, cables 412B may be configured to extend an electrical connection to battery assembly 400B. Cables 412B may include a conductive element. A conductive element may include but is not limited to, lead, zinc, copper, carbon, cadmium, nickel oxide hydroxide, iron, manganese dioxide, vanadium, lithium, sodium, lithium iron phosphate, nickel cobalt aluminum oxide, lithium manganese oxide, lithium titanite, nickel manganese cobalt oxide, lithium sulfur, and/or zinc bromine.

Referring now to FIG. 4C, an exemplary embodiment of wearable circuit system 400C in a relaxed position is illustrated. Wearable circuit system 400C may include flexible connection device 408C. Flexible connection device 408C may be configured to be in a curved position not stretched to maximum length potential. In some embodiments, wearable circuit system 400C may include battery assembly 412C. Battery assembly 412C may be configured to provide an electrical power source to an external component of wearable circuit system 400C. In some embodiments, battery assembly 412C may be configured to store power in the form of electrical energy. In some embodiments, wearable circuit system 400C may include substrate 404C. Substrate 404C may include a soft substrate such as rubber, fabric, and the like. In some embodiments, battery assembly 412C and flexible connecting device 408C may be configured to be encapsulated in substrate 404C.

Figure 4D:
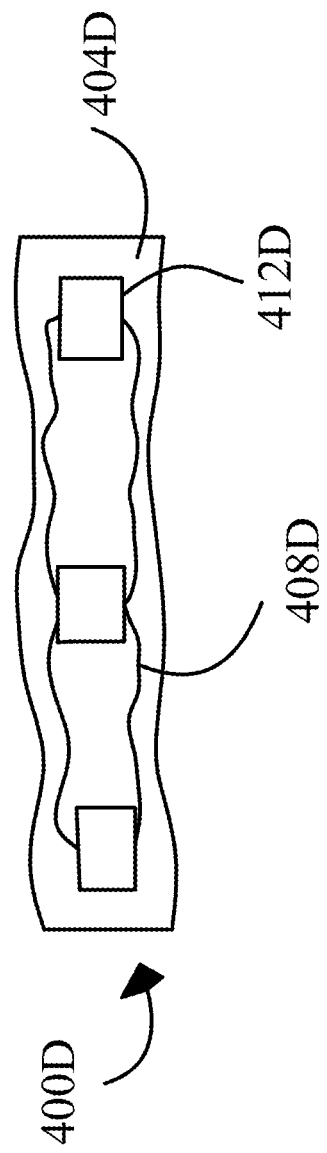

Referring now to FIG. 4D, an exemplary embodiment of wearable circuit system 400D in a stretched position is illustrated. In some embodiments, wearable circuit system 400D may include battery assembly 412D. In some embodiments, wearable circuit system 400D may include substrate 404D. In a stretched position, flexible connecting device 408D may be pulled taught and become more linear in shape. In such an instance, the thickness of an insulating outer lay located on flexible connecting device 408D may become thinner as flexible connecting devices 408D are pulled more taught. Wearable circuit system 400D may be configured to be stretched into a taught stretched position based on numerous factors including various charges and/or electrical accommodations of battery cells, as well as textile, material, and/or device that wearable circuit system 400D may be incorporated into.

Figure 4E:
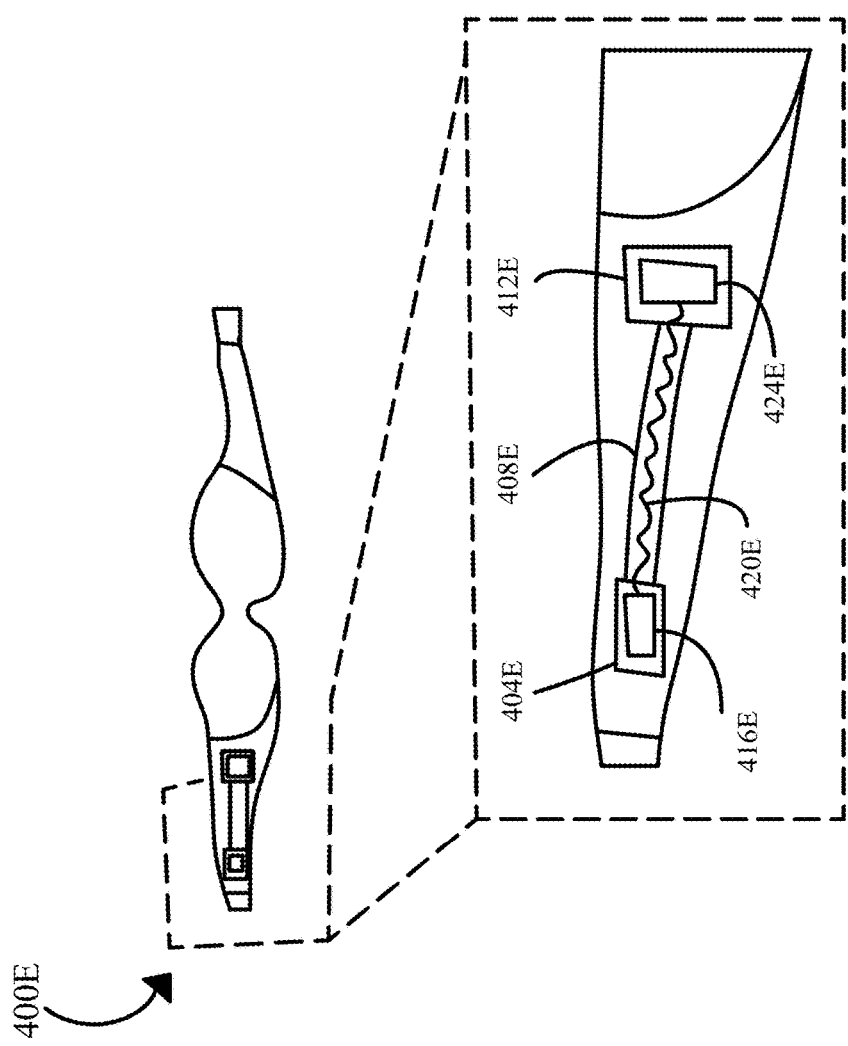

Referring now to FIG. 4E, an exemplary embodiment of implanting wearable circuit system 400E into a garment, such as a brassier is illustrated. In some embodiments, wearable circuit system 400E may include two battery cells or battery packs interspaced by flexible connecting device 420E of varying length. In some embodiments, wearable circuit system 400E may include a first battery assembly 416E. First battery assembly 416E may be configured to be encapsulated by encapsulation 404E. In some embodiments, encapsulation 404E may include a material such as elastomer. In some embodiments, flexible connecting device 420E may not contain an insulating outer layer composed on a textile encapsulation and/or no encapsulation. In some embodiments, flexible connecting device 420E may be connected directly to a textile and/or garment, such as the brassier illustrated above. In some embodiments, wearable circuit system 400E may include a second encapsulation 408E. Second encapsulation 408E may be configured to encapsulate flexible connecting device 420E. In some embodiments, flexible connecting device 420E may be configured to be fully encapsulated by second encapsulation layer 408E. In some embodiments, wearable circuit system 400E may include a second battery assembly 424E. Second battery assembly 424E may be encapsulated by third encapsulation layer 412E. In some embodiments, second battery assembly 424E may be configured to connect to flexible connecting device 420E. In some embodiments, flexible connecting device 420E may be configured to provide an electrical connection between first battery assembly 416E and second battery assembly 424E. In some embodiments, flexible connecting device 420E may be configured to transmit power between first battery assembly 416E and second battery assembly 424E. In some embodiments, flexible connecting device 420E may stretch along a path of a garment while providing an electrical connection between first battery assembly 416E and second battery assembly 424E. In some embodiments, encapsulation layers 404E, 408E, and 412E may include the same material. In some embodiments, encapsulation layers 404E, 408E, and 412E may include different materials based on a garment, size of battery assemblies, type of garment material, thermal energy management, and/or other factors.

Figure 4F:
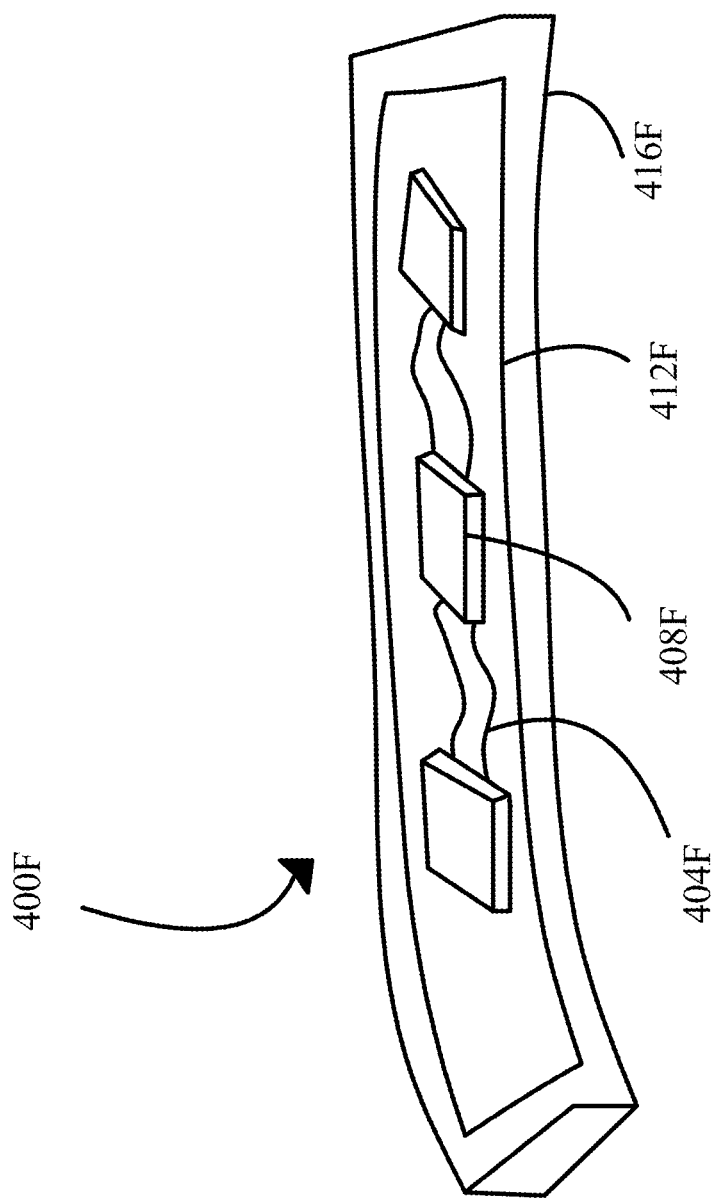

Referring now to FIG. 4F, an exemplary embodiment of a first battery assembly 408F including a flexible printed circuit board 412F is illustrated. In an embodiment, flexible printed circuit board 412F may be flexible and bendable. In some embodiments, flexible printed circuit board 412F may be configured to be rigid in a horizontal direction. In some embodiments, flexible printed circuit board 412F may be configured to be flexible in a horizontal direction. In some embodiments, first battery assembly 408F may be soldered directly onto flexible printed circuit board 412F. Flexible circuit board 412F may include a wearable circuit system that may be wholly encapsulated with a material such as a soft substrate, as described above in more detail in reference to FIG. 1A. In such an instance, flexible printed circuit board 412F may function as a battery holder.

Figure 5:
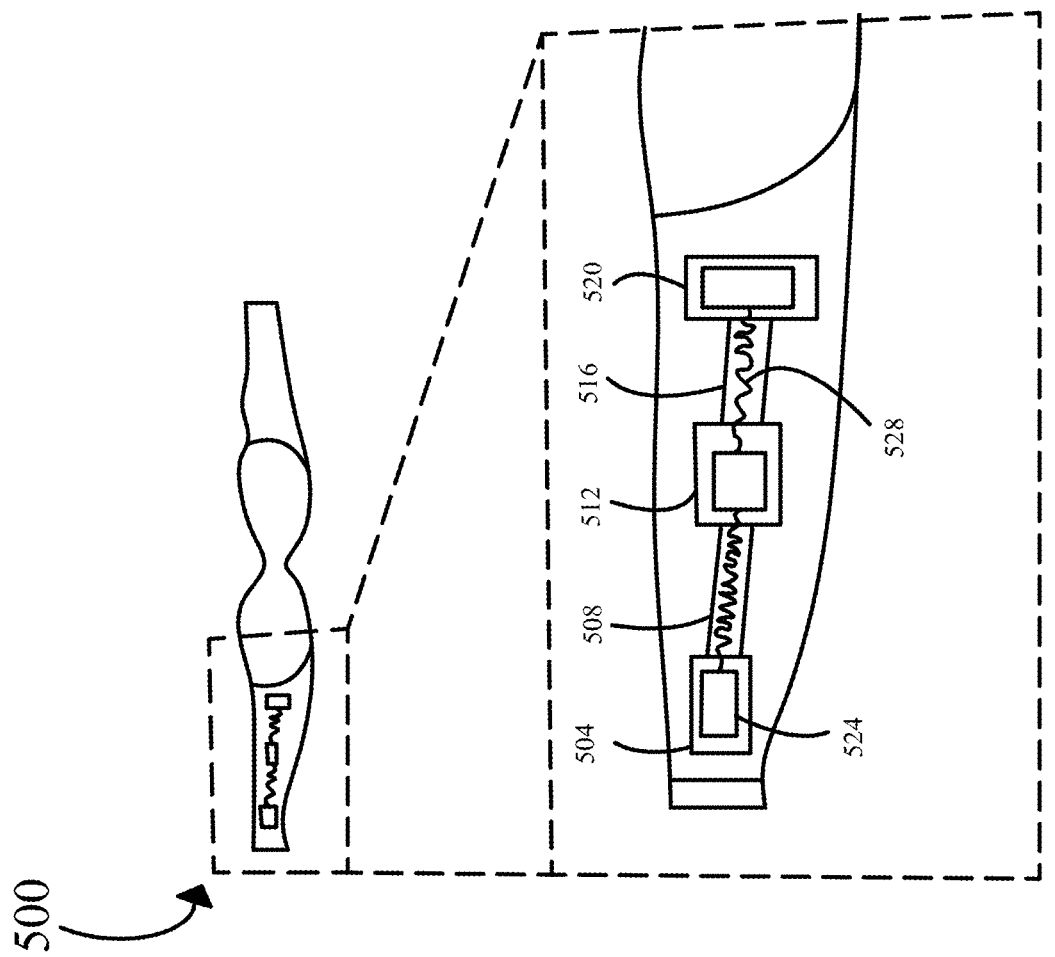
FIG. 5 is an exemplary embodiment of a wearable circuit incorporated into a textile.

Referring now to FIG. 5, an exemplary embodiment wearable circuit system 500 incorporated into a textile is illustrated. In some embodiments, wearable circuit system 500 may include a battery assembly 524. In some embodiments, battery assembly 524 may be encapsulated in first encapsulate 504. In some embodiments, wearable circuit system 500 may include a second encapsulation 508. In some embodiments, wearable circuit system 500 may include a third encapsulate 512. In some embodiments, wearable circuit system 500 may include a fourth encapsulate 516. In some embodiments, wearable circuit system 500 may include a fifth encapsulate 520. In some embodiments, each encapsulate of wearable circuit system 500 may be configured to include a water resistant and/or waterproof material. In some embodiments, an encapsulate of wearable circuit system 500 may include an elastomer. Each encapsulate of wearable circuit system 500 may be configured to attach a component of wearable circuit system 500 to a substrate. A substrate may include a fabric. In some embodiments, a fabric may include a bra. In some embodiments, encapsulates may be configured to have a varying degree of thickness so as to uniformly align with a fabric. In some embodiments, encapsulates may be configured to have a plurality of dimensions. A plurality of dimensions may include dimensions configured to fully encapsulate a component of wearable circuit system 500 in an encapsulate. In some embodiments, encapsulate 508 may be configured to surround a flexible connecting device. In some embodiments, encapsulate 508 may be configured to incorporate a flexible connecting device into a fabric. In some embodiments, encapsulate 508 may be configured to partially incorporate a flexible connecting device into a fabric. In some embodiments, encapsulate 508 may be configured to prevent unwanted contact to a flexible connecting device from, as a non-limiting example, human skin. In some embodiments, encapsulate 508 may be configured to be thin enough such that a user would not notice a component of wearable circuit system 500. In some embodiments, wearable circuit system 500 may include a plurality of battery assemblies configured to be encapsulated and incorporated into a fabric. In some embodiments, wearable circuit system 500 may include three battery assemblies encapsulated and incorporated into a fabric. In some embodiments, wearable circuit system 500 may include a sensor. A sensor may include a heartbeat, EKG, thermal, ultrasound, or other sensor. In some embodiments, a sensor may be configured to be encapsulated in an encapsulate of wearable circuit system 500. In some embodiments, an encapsulate of wearable battery assembly 500 may be configured to incorporate a sensor into a fabric. In some embodiments, wearable battery assembly 500 may include a wireless transmitting device.

In an embodiment and with continued reference to FIG. 5, a first battery assembly 524 may be connected to one or more electronic components using one or more flexible connecting devices 528. In an embodiment, wearable circuit system 500 may include a connection to one or more electronic components using a serpentine power connection. In some embodiments, each component of wearable circuit system 500 may contain a soft encapsulation. In some embodiments, components of wearable circuit system 500 may be distributed across one wing of a brassier, which may conform to the shape of a human body when worn and may be wrapped around at various locations around the torso. In an embodiment, wearable circuit system 500 may be placed and/or distributed anywhere in a textile and may provide flexible, and flexible interconnectivity using one or more flexible connecting devices 528. Flexible interconnectivity may provide greater power capacity of a textile, than the textile itself. Flexible connecting devices 528 may have varying geometries and thickness as described above in more detail in reference to FIG. 2.

Figure 6:
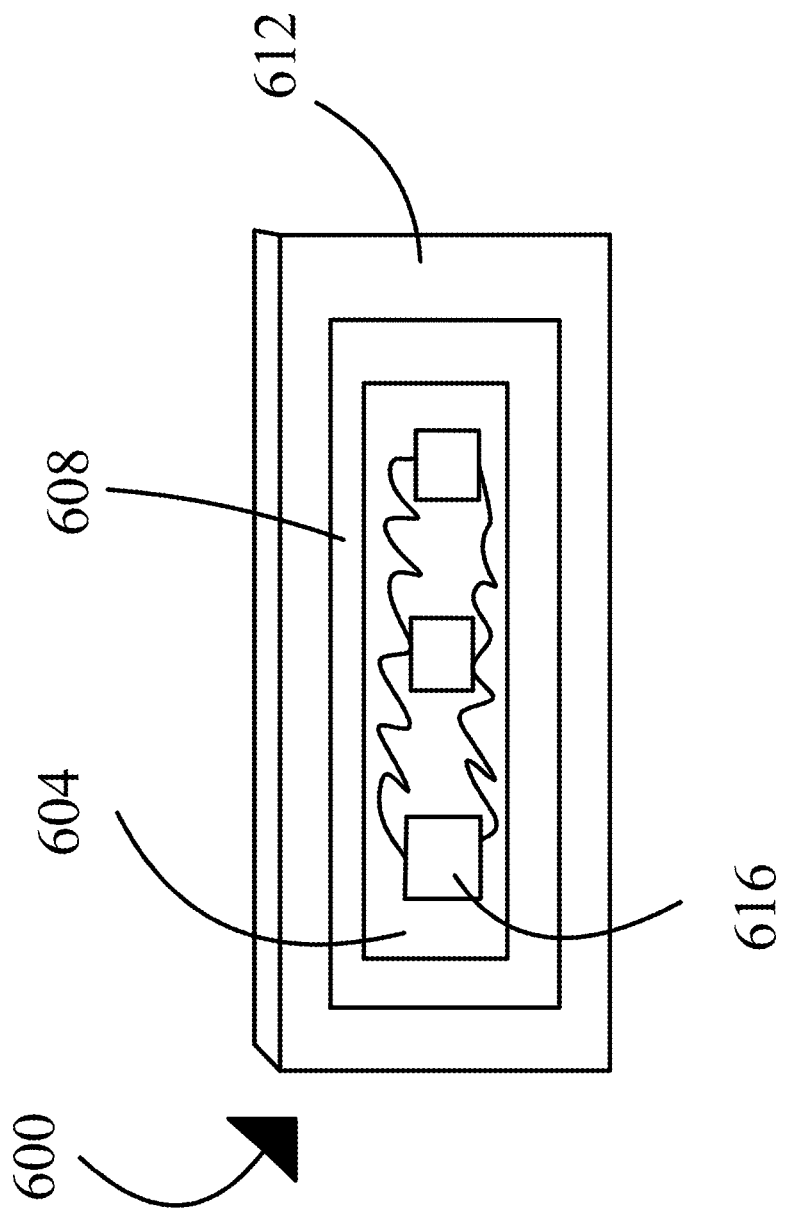
FIG. 6 is an exemplary embodiment of soft substrate.

Referring now to FIG. 6, an exemplary embodiment of wearable circuit system 600 is illustrated. In some embodiments, wearable circuit system 600 may include a plurality of layers of soft substrate. In some embodiments, wearable circuit system 600 may include a battery assembly 616. In some embodiments, wearable circuit system 600 may include a first encapsulation layer 604. In some embodiments, wearable circuit system 600 may include a second encapsulation layer 608. In another embodiment, wearable circuit system 600 may include a third encapsulation layer 612. In some embodiments, each encapsulation layer may be configured to be equidistant from one another. In other embodiments, each encapsulation layer may be configured to have varying distances between one another. In some embodiments, four or more encapsulation layers may be included in wearable circuit system 600. In some embodiments, each encapsulation layer may be configured to provide an extra layer of structural support to battery assembly 616. Each layer may include any of the materials as described above in more detail in reference to FIG. 1A.

Figure 7:
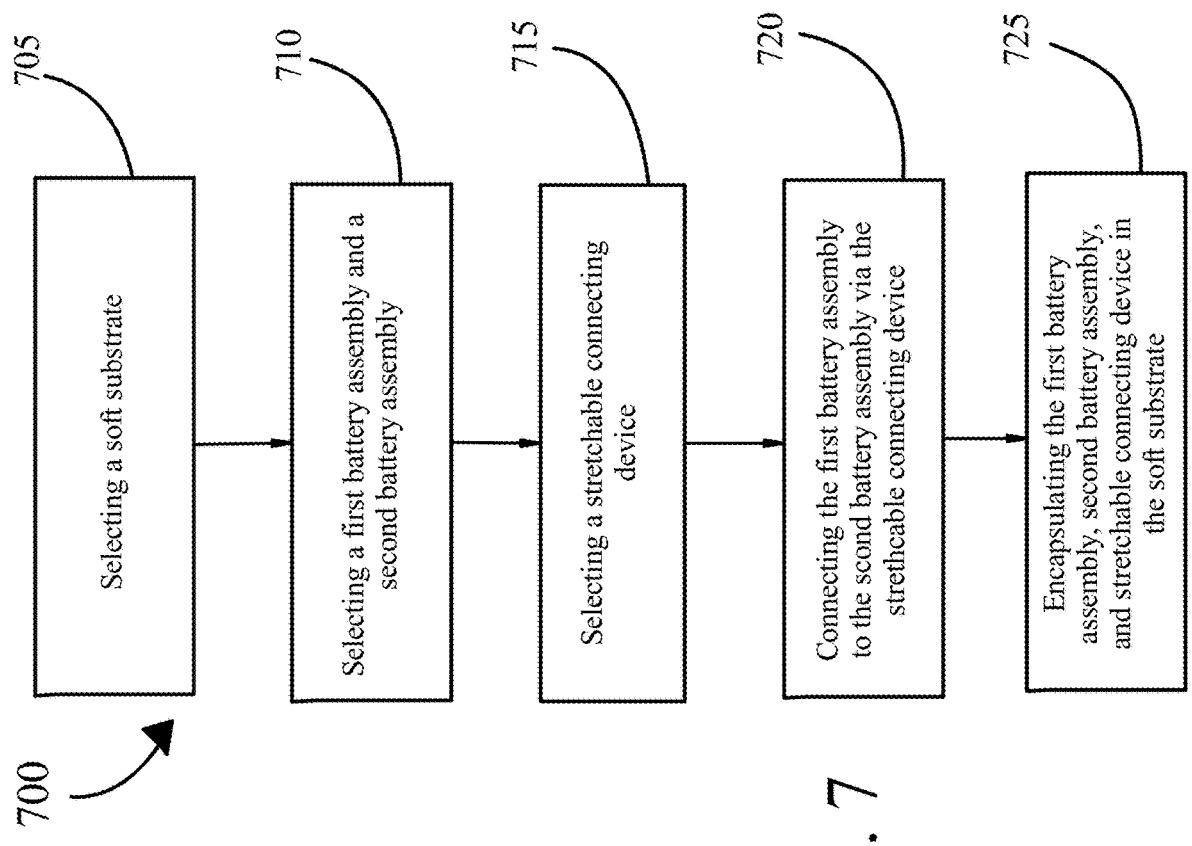
FIG. 7 is a process flow diagram illustrating an exemplary embodiment of a method of manufacturing a wearable circuit system.

Referring now to FIG. 7, an exemplary embodiment 700 of a method of manufacturing a wearable circuit is illustrated. At step 705, a soft substrate is selected. A soft substrate may include a material that may be easy to mold and shape. In some embodiments, a soft substrate may be configured to be soft to the touch. A soft substrate may include but is not limited to rubber, silicone, woven fiber, polymers, granular materials and/or foam. A soft substrate may include a washable material. In some embodiments, a soft substrate may include a flexible material. A flexible material may be configured to be capable of being modified to respond to altered circumstances and/or altered conditions. A soft substrate may include a waterproof material that may be configured to be impervious to liquids, such as water. In some embodiments, a soft substrate may include a uniform thickness. In other embodiments, a soft substrate may include a varying thickness. In some embodiments, a soft substrate may include a textile. A textile may include intimate apparel including but not limited to, a bra, underwear, sports bra, bralette, mastectomy bra, brassier, nursing bra, strapless bra, balconette bra, t-shirt bra, racerback bra, wireless bra, stick on bra, push up bra, unlined bra, maternity bra, bandeau bra, longline bra, halter bra, plunge bra, demi bra, full coverage bra, padded bra, underwire bra, convertible bra, pantyhose, swimwear, underwear, body shapeware, thong, corset, pajamas, boxer shorts, briefs, knickers, t-shirt, sleeveless shirts, singlets, tank tops, camisole, basque, bodice torsolette, and the like. A textile may include for example an item of clothing such as a shirt, pant, hat, underwear, bra, headband, skirt, dress, socks, jumpsuit, sleepwear, swimwear, exercise clothes, and the like. A textile may include an appliance such as a watch, car interior, rug, chair, and/or any item containing textiles.

Referring still to FIG. 7, at step 710, a first battery assembly and a second battery assembly are selected. A battery assembly may include an electrochemical cell. An electromechanical cell may include any device capable of generating electrical energy from a chemical reaction and/or using electrical energy to cause a chemical reaction. An electromechanical cell may include a coin battery, a cylinder battery, a primary battery, a secondary battery, a wet cell battery, a dry cell battery, a molten salt battery, a reserve battery, a rechargeable battery, and the like. An electromechanical cell may accommodate various capacity electric charges, to deliver various rated voltage, including for example satisfying various voltage, capacity and/or discharge current requirements. In a non-limiting example, an electromechanical cell may supply power at 1.5V. In yet another non-limiting example, an electromechanical cell may supply power at 3V or 9V. A battery assembly may include a container. A container may be configured to house components of an electromechanical cell. A battery assembly may include a separator. A separator may include a non-woven fibrous fabric that separates electrodes. A battery assembly may include an electrolyte. An electrolyte may include a medium that may cause a movement of ions within the battery assembly. A battery assembly may contain an anode electrode through which electrons may be discharged, and a cathode electrode through which electrons may be charged. A battery assembly may include a collector. A collector may include a pin such as a brass pin that conducts electricity to an outside circuit. A first and second battery assembly may be selected based on a plurality of reasons such as, but not limited to, size, shape, power capacity, power output, weight, and the like. In some embodiments, a first battery assembly may be selected to have different dimensions and/or power outputs than a second battery assembly. In some embodiments, a first battery assembly and a second battery assembly may be configured to have the same dimensions and/or power outputs. In some embodiments, a plurality of battery assemblies may be selected. In some embodiments, a plurality of battery assemblies may include three or more battery assemblies.

Referring still to FIG. 7, at step 715, a flexible connecting device is selected. A flexible connecting device may include an electrically conductive core material surrounded by an insulating outer layer. An electrically conductive core material may include any material suitable for use as an electrically conductive element as described above in more detail. An electrically conductive core may include material at the central location of a flexible connecting device. An electrically conductive core may include a single, cylindrical, and/or flexible strand or rod containing an electrically conductive element. An electrically conductive core may include a plurality of filament conductors. Filament conductors may include two or more strands wrapped and/or bundled together to form a larger conductive element. One or more strands may be woven together and/or braided together loosely and/or optionally combined with an elastic, and/or any material that may enable the strands to retain elasticity. For instance and without limitation, an electrically conductive core may include seven strands of wire, containing one in the middle with six wires surrounding the middle wire, all in close contact. Filament conductors may be fused together, such as for example, perfused wire. Filament conductors may be braided together, containing wires that are braided into one larger conductive element. An electrically conductive core may be surrounded by an insulating outer layer. An insulating outer lay may include a material that has low electrical connectivity. An insulating outer layer may be composed of one or more materials such as plastic, including for example, polyethylene, and/or polyurethane. In an embodiment, a flexible connecting device may be configured to act as a battery holder. In an embodiment, a flexible connecting device may include a flexible printed circuit board, and/or a conductive textile. In yet another non-limiting example, a flexible connecting device may include a wire containing one or more flexible printed circuit board connectors. In some embodiments, a plurality of flexible connecting devices may be selected. In some embodiments, a flexible connecting device may allow for a wearable circuit to configure to varying geometries of a human body when incorporated into a garment. In some embodiments, a flexible connecting device may allow for one or more battery to be stretched and/or compressed to accommodate varying angles, textiles, garments, and/or placements on a human body. In some embodiments, a flexible connecting device may be selected to include a specific stretchability. In some embodiments, a flexible connecting device may be selected to include a stretchability that may best suite a textile. A flexible connecting device may be selected to have a more rigid structure, such that it does not stretch greatly from a resting position. In some embodiments, a flexible connecting device may be selected to have great stretchability, such that it is able to stretch a great length from a resting position.

Referring still to FIG. 7, at step 720, the first battery assembly is connected to the second battery assembly via the flexible connecting device. In some embodiments, a flexible connecting device may be configured to connect a plurality of battery assemblies. In some embodiments, a flexible connecting device may be configured to connect a first battery assembly to a second battery assembly in a series connection. In some embodiments, a flexible connecting device may be configured to connect a first battery assembly to a second battery assembly in a parallel connection. In some embodiments, a connection between a first battery assembly and a second battery assembly may include an electrical communication. An electrical communication may include power transmission, data transmission, and the like.

Referring still to FIG. 7, at step 725, the first battery assembly, second battery assembly, and flexible connecting device are encapsulated in the soft substrate. In some embodiments, a portion of the first battery assembly, second battery assembly, and flexible connecting device may be encapsulated in a soft substrate. In other embodiments, a portion of the first battery assembly, second battery assembly, and flexible connecting device may be configured to be fully encapsulated into a soft substrate. In some embodiments, encapsulation may include surrounding a surface of the first battery assembly, second battery assembly, and flexible connecting device with a soft substrate. In some embodiments, encapsulation may include a single layer of encapsulate. In other embodiments, a plurality of layers may encapsulate a first battery assembly, second battery assembly, and flexible connecting device. In some embodiments, each layer of encapsulate may be configured to be stacked upon one another. In other embodiments, each layer of encapsulate may be configured to be applied to a component of a wearable circuit. In a non-limiting example, a first encapsulate may be placed on a first battery assembly, a second encapsulate may be placed on a second battery assembly, and a third encapsulate may be placed on a flexible connecting device. In some embodiments, each encapsulate may include the same material. In other embodiments, each encapsulate may include a different material. In some embodiments, multiple layers of encapsulate may be applied to a first battery assembly, second battery assembly, and/or flexible connecting device. In some embodiments, an encapsulate may be heated to allow the encapsulate to surround a component of a wearable circuit system better, such as a first battery assembly, second battery assembly, and/or flexible connecting device. In some embodiments, an encapsulate may include a combination of materials. In some embodiments, an encapsulate may include a single material, such as elastomer.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, and apparatus according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for a wearable circuit, the system comprising:
a soft substrate;
a first battery assembly attached to the soft substrate;
a second battery assembly attached to the soft substrate;
a flexible connecting device, wherein the flexible connecting device is configured to:
connect the first battery assembly to the second battery assembly; and
stretch along a path of the soft substrate;
wherein the flexible connecting device provides an electrical connection between the first and second battery assemblies while being stretched.

2. The system of claim 1, wherein the soft substrate includes a fabric.

3. The system of claim 1, wherein the first battery assembly, second battery assembly, and flexible connecting device are encapsulated in the soft substrate.

4. The system of claim 1, wherein the soft substrate includes a garment worn around a torso.

5. The system of claim 1, wherein the first and second battery assemblies are configured to be in a stacked arrangement.

6. The system of claim 1, wherein the first battery assembly is configured to house the flexible connecting device.

7. The system of claim 1, wherein the first battery assembly includes a mechanical battery holder.

8. The system of claim 1, wherein the flexible connecting device is configured to be compressed along a path of the soft substrate.

9. The system of claim 1, wherein the flexible connecting device includes a conductive core material surrounded by an insulating outer layer.

10. The system of claim 1, wherein the flexible connecting device is configured to provide multiple electrical connections to a plurality of battery assemblies.

11. A method of fabricating a wearable circuit, the method comprising:
- selecting, a soft substrate;
- selecting, a first battery assembly and a second battery assembly;
- selecting, a flexible connecting device, the flexible connecting device configured to:
  - provide an electrical connection between the first battery assembly and second battery assembly; and
  - stretch along a path of the soft substrate;
- connecting, the first battery assembly to the second battery assembly via the flexible connecting device; and
- encapsulating the first battery assembly, second battery assembly, and flexible connecting device in the soft substrate.

12. The method of claim 11, wherein the soft substrate includes a fabric.

13. The method of claim 11, wherein the soft substrate includes a garment worn around a torso.

14. The method of claim 11, wherein the flexible connecting device is configured to compress along a path of the soft substrate.

15. The method of claim 11, wherein the first battery assembly is configured to house the flexible connecting device.

16. The method of claim 11, wherein the flexible connecting device includes a conductive core material surround by an insulating outer layer.

17. The method of claim 11, wherein the flexible connecting device is further configured to provide multiple connections to a plurality of battery assemblies.

18. The method of claim 11, wherein the first battery assembly includes a mechanical battery holder.

19. The method of claim 11, wherein the first battery assembly, second battery assembly, and flexible connecting device are encapsulated in the soft substrate.

20. The method of claim 11, wherein the flexible connecting device includes a printed circuit board.

* * * * *